(12) United States Patent
Chen et al.

(10) Patent No.: US 10,983,077 B2
(45) Date of Patent: Apr. 20, 2021

(54) DETERMINING THE OLEOPHILIC TO AQUEOUS PHASE FLUID RATIO FOR DRILLING FLUIDS

(71) Applicant: Halliburton Energy Services, Inc., Houston, TX (US)

(72) Inventors: Songhua Chen, Katy, TX (US); Magdalena Traico Sandor, Humble, TX (US); Cato Russell McDaniel, Montgomery, TX (US); Jason Glen Bell, Kingwood, TX (US); William W. Shumway, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 248 days.

(21) Appl. No.: 15/540,553

(22) PCT Filed: Jan. 29, 2015

(86) PCT No.: PCT/US2015/013535
§ 371 (c)(1),
(2) Date: Jun. 28, 2017

(87) PCT Pub. No.: WO2016/122531
PCT Pub. Date: Aug. 4, 2016

(65) Prior Publication Data
US 2018/0003654 A1    Jan. 4, 2018

(51) Int. Cl.
*G01N 24/08* (2006.01)
*G01V 3/14* (2006.01)
(Continued)

(52) U.S. Cl.
CPC .......... *G01N 24/082* (2013.01); *E21B 49/08* (2013.01); *G01N 24/081* (2013.01);
(Continued)

(58) Field of Classification Search
CPC .......... G01V 3/32; G01V 3/14; G01N 24/081; G01N 24/082; G01N 33/2847;
(Continued)

(56) References Cited

U.S. PATENT DOCUMENTS 6,084,408 A       7/2000  Chen et al.
6,140,817 A  *  10/2000  Flaum ................ G01V 3/32
                                                                324/303
(Continued)

FOREIGN PATENT DOCUMENTS

FR     2864241        6/2005
WO    2008103635    8/2008
WO    2014133537    9/2014

OTHER PUBLICATIONS

International Search Report & Written Opinion for PCT Application No. 15013535 dated Sep. 11, 2015.
(Continued)

*Primary Examiner* — Huy Q Phan
*Assistant Examiner* — Dustin R Dickinson
(74) *Attorney, Agent, or Firm* — Tenley Krueger; C. Tumey Law Group PLLC

(57) ABSTRACT

A method for monitoring the oleophilic fluid to aqueous fluid ratio of a drilling fluid includes selecting a sample of the drilling fluid that has been recirculated, measuring the NMR response of the sample of the drilling fluid and determining the oleophilic fluid to aqueous fluid ratio of the drilling fluid based at least in part on the NMR response.

18 Claims, 4 Drawing Sheets

(51) Int. Cl.
*G01R 33/30* (2006.01)
*E21B 49/08* (2006.01)
*G01N 33/28* (2006.01)

(52) U.S. Cl.
CPC ............ *G01R 33/307* (2013.01); *G01V 3/14* (2013.01); *G01N 33/2847* (2013.01)

(58) Field of Classification Search
CPC ... G01N 33/2823; E21B 49/08; E21B 49/084; E21B 2049/085; G01R 33/50
See application file for complete search history.

(56) References Cited

U.S. PATENT DOCUMENTS

| | | | |
|---|---|---|---|
| 6,178,807 B1 * | 1/2001 | Baldwin | G01N 15/082 324/376 |
| 6,316,940 B1 | 11/2001 | Akkurt | |
| 6,346,813 B1 * | 2/2002 | Kleinberg | G01N 24/081 324/303 |
| 6,366,087 B1 | 4/2002 | Coates et al. | |
| 6,765,380 B2 | 7/2004 | Freedman et al. | |
| 6,833,699 B2 | 12/2004 | Galford et al. | |
| 6,927,014 B1 | 8/2005 | Figov | |
| 6,933,719 B2 | 8/2005 | Thomann et al. | |
| 7,053,611 B2 | 5/2006 | Freedman | |
| 7,091,719 B2 | 8/2006 | Freedman | |
| 7,253,617 B1 | 8/2007 | Chen et al. | |
| 7,298,142 B2 | 11/2007 | Hursan et al. | |
| 7,363,161 B2 | 4/2008 | Georgi et al. | |
| 7,372,264 B2 | 5/2008 | Akkurt et al. | |
| 7,603,237 B2 | 10/2009 | Heaton et al. | |
| 7,768,260 B2 | 8/2010 | Chen et al. | |
| 7,888,933 B2 | 2/2011 | Minh | |
| 8,076,933 B2 | 12/2011 | Freedman | |
| 8,400,147 B2 | 3/2013 | Anand et al. | |
| 8,653,815 B2 | 2/2014 | Chanpura et al. | |
| 2003/0128032 A1 | 7/2003 | Heaton et al. | |
| 2003/0214286 A1 * | 11/2003 | Heidler | G01N 24/081 324/303 |
| 2005/0221495 A1 | 10/2005 | Bell et al. | |
| 2006/0164084 A1 | 7/2006 | Lomnes | |
| 2009/0255669 A1 * | 10/2009 | Ayan | E21B 33/1243 166/250.15 |
| 2010/0283459 A1 | 11/2010 | Kruspe et al. | |
| 2010/0315081 A1 | 12/2010 | Chanpura et al. | |
| 2011/0181278 A1 | 7/2011 | Chen et al. | |
| 2012/0013335 A1 | 1/2012 | Saasen et al. | |
| 2012/0241149 A1 * | 9/2012 | Chen | G01V 3/32 166/250.01 |
| 2013/0103627 A1 * | 4/2013 | Maddinelli | G01N 24/081 706/21 |
| 2013/0233619 A1 * | 9/2013 | Ramamoorthy | G01V 5/04 175/50 |
| 2013/0271127 A1 | 10/2013 | Dangfa et al. | |
| 2013/0325348 A1 | 12/2013 | Valori et al. | |
| 2013/0325408 A1 | 12/2013 | Song | |
| 2014/0033815 A1 | 2/2014 | Oraby | |
| 2014/0035574 A1 | 2/2014 | Sun et al. | |
| 2014/0132259 A1 | 5/2014 | Song | |
| 2014/0145716 A1 | 5/2014 | Dirksen et al. | |
| 2014/0253116 A1 | 9/2014 | Freedman et al. | |
| 2015/0168585 A1 * | 6/2015 | Bennett | G01V 3/32 324/303 |

OTHER PUBLICATIONS

"Nuclear Magnetic Resonance Petrophysical and Logging Applications" by Dunn et al. Published in Jan. 2002.
"Magnetic Susceptibility Contrast Effects on NMR T2 Logging" by LaTorraca et al. Published in Jun. 1995.
"Wettability effects in a sandstone reservoir and outcrop cores from NMR relaxation time distributions" by Guan et al. Published in Jun. 2002.
"The Downhole NMR (Nuclear Magnetic Resonance) Fluid Analyzer" by Prammer et al. Published in Dec. 2001.

* cited by examiner

DETERMINING THE OLEOPHILIC TO AQUEOUS PHASE FLUID RATIO FOR DRILLING FLUIDS

BACKGROUND

Provided are systems and methods for monitoring the oleophilic to aqueous phase fluid ratio of drilling fluids. More particularly, systems and methods may be provided for a nuclear magnetic resonance analysis method for measuring the oleophilic to aqueous phase fluid ratio of drilling fluids and/or shifts in the oleophilic to aqueous phase fluid ratio of drilling fluids that have been circulated in a wellbore During the drilling of a wellbore into a subterranean formation, a drilling fluid, also referred to as a drilling mud, may be continuously circulated from the surface down to the bottom of the wellbore being drilled and back to the surface again. The drilling fluid serves several functions, one of them being to transport wellbore cuttings up to the surface where they are separated from the drilling fluid. Another function of the drilling fluid is to provide hydrostatic pressure on the walls of the drilled wellbore so as to prevent wellbore collapse and the resulting influx of gas or liquid from the formations being drilled. For these and other reasons, it can be important to precisely know the characteristics and chemical composition of the drilling fluid.

Determining oleophilic to aqueous phase fluid ratio of a drilling fluid may be beneficial to an efficient drilling operation. The oleophilic to aqueous phase fluid ratio allows operators of a drilling operation to determine the fluid rheology, the impact the drilling fluid may have on the formation, the salinity of the drilling fluid, density, filtration characteristics or requirements, etc. For example, a fluid that is too viscous may reduce drilling efficiency; conversely a fluid that is not viscous enough may leach out to the formation and lost. A correctly formulated and maintained drilling fluid composition may be beneficial to maintain the filter cake and to ensure that drill solids, such as drill cuttings, make it to the surface.

Typically, oleophilic to aqueous phase fluid ratio has been measured using a technique called a retort. A retort uses a distillation unit to heat and then distill the oleophilic phase and aqueous phase. The volume fraction of each is then compared to the original known volume used during formulation of the drilling fluid in order to measure the changes to the drilling fluid during use. This process can take an hour or more and is not automated. Further, the lag in providing feedback makes modeling the downhole environment more difficult and less precise. As such, the retort process is slower to perform and also provides measurements that lag relative to operational performance. This in turn may lead to delayed correction of the drilling fluid and a reduction in the overall efficiency of the operation. Further, retort analysis with some salts, e.g., nitrates and formates, may be dangerous and potentially cause an explosion, thus precluding the use of retort analysis in these specific formulations.

BRIEF DESCRIPTION OF THE DRAWINGS

These drawings illustrate certain aspects of some examples of the present invention, and should not be used to limit or define the invention.

DETAILED DESCRIPTION

Figure 1:
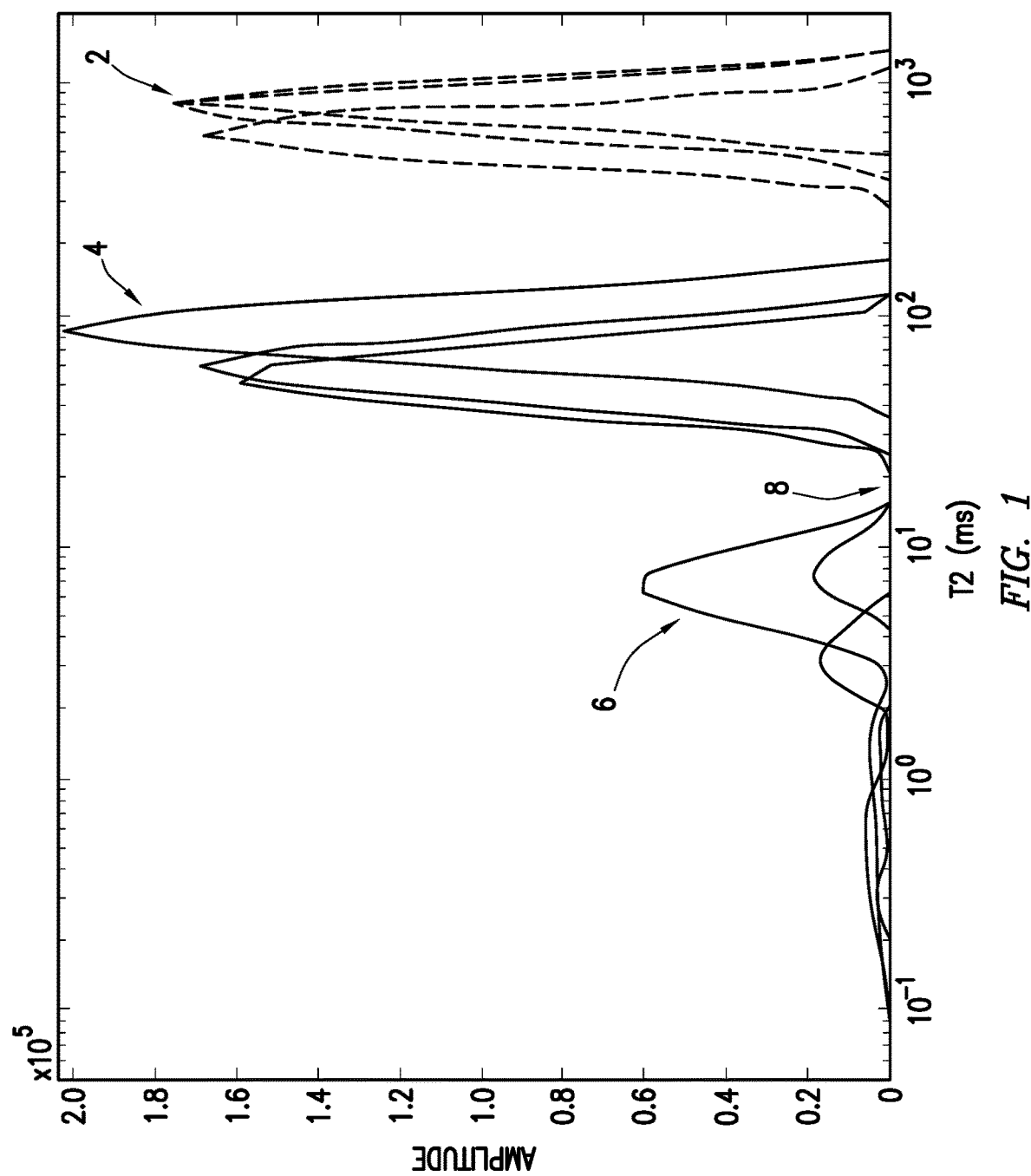
FIG. 1 illustrates example the spin-spin relaxation time distributions for three emulsified oils and three base oils.

Provided are systems and methods for monitoring the oleophilic to aqueous phase fluid ratio of drilling fluids. More particularly, systems and methods may be provided for a nuclear magnetic resonance analysis method for measuring the oleophilic to aqueous phase fluid ratio of drilling fluids and/or shifts in the oleophilic to aqueous phase fluid ratio of drilling fluids that have been circulated in a wellbore.

As disclosed below, systems and methods may be provided for determining the oleophilic to aqueous phase fluid ratio of drilling fluids. In some examples, the drilling fluids may comprise various additives such as emulsifiers, viscosifiers, density modifiers, fluid loss control additives, thinners, lost circulation materials, lubricants, corrosion inhibitors, hydrogen sulfide scavengers, salts, etc., and combinations thereof. The drilling fluid may be an invert emulsion, where the oleophilic phase may comprise the continuous phase and the aqueous phase may comprise the internal phase. With any drilling fluid, the ratio of the oleophilic phase to the aqueous phase ("O/A ratio") should be maintained carefully so as to provide a strong, stable drilling fluid. Since the oleophilic phase and the aqueous phase may have different NMR responses, an NMR analysis of the drilling fluid may be prepared and used to determine the O/A ratio of the drilling fluid. However, as discussed above, this analysis may be complicated in situations where the oleophilic phase and the aqueous phase comprise overlapping NMR responses. Advantageously, the systems and methods disclosed herein may allow an operator or an automated process to quickly and efficiently ascertain a drilling fluid's O/A ratio. Further, the compositional makeup of the drilling fluid may be adjusted to counter changes from exposure to the formation or to anticipate changes in the formation that will occur as drilling continues.

The NMR response for both oleophilic and aqueous phases may be different from the bulk water and base oil by a number of factors. First, to improve drilling fluid performance, various additives, soluble with either the oleophilic phase or the aqueous phase, may be introduced to the drilling fluid. These additives may include salts, emulsifiers, viscosifiers, oil-wetting agents, weighting agents, bridging agents, and mud cake inhibitors, among others. These additives may change the relaxation times and diffusivities of the aqueous and oleophilic phases in comparison to their respective pure states. Second, the presence of solids in the drilling fluid creates a surface area that is in contact with fluid molecules. Fluid molecules that wet the solid surface may have enhanced relaxation to much greater extent than fluid molecules that are non-wetting to the solid surface. Furthermore, the presence of solids reduces the free volume where fluid molecules can diffuse freely, thereby potentially causing the restricted diffusion effect. Restricted diffusion can be enhanced with a higher solid concentration. Third, a drilling fluid in the form of a water-in-oil emulsion may create an additional barrier for water to have contact with a solid surface, while also exposing oil molecules to the surface of the solids. If the oil-wetting agents promote oil molecules to have stronger interaction with the solid surface molecules, a reduction of the oil relaxation time would be expected. On the other hand, the diffusion of protons in the water-in-oil emulsion may also be restricted and can depend on the emulsion size distribution.

Therefore, the proton relaxation times and the diffusivities of the aqueous and oleophilic phases that may be present in drilling fluids, such as emulsified oil-based drilling fluids, may not be the same as that in their bulk fluid states and also are generally different from oil and water in porous rock. To illustrate the different NMR responses of the oleophilic and aqueous phases of drilling fluids from their bulk fluid states, NMR responses were measured for various drilling fluids and their corresponding base oils. FIG. 1 shows example NMR proton spin-spin relaxation time ($T_2$) distribution measurements at 2 MHz of three emulsified oil-based drilling fluids and their corresponding base oil measurements. The relaxation time distribution measurements of the emulsified oil-based drilling fluids are plotted with solid curves while the relaxation time distribution measurements of the corresponding base oils are plotted with dashed curves. The major peaks of the $T_2$ relaxations for the base oil are shown at reference number 2. The major peaks of the $T_2$ relaxations for the oleophilic phase of emulsified drilling fluids are shown at reference number 4. The major peaks of the $T_2$ relaxations for the aqueous phase of the emulsified drilling fluids are shown at reference number 6. The measurements were performed at ambient conditions (1 atm, 25° C.). As a reference, tap water at these conditions has a $T_2$ relaxation of about 2.5 seconds at these conditions.

As can be seen in FIG. 1, the $T_2$ relaxations of both the aqueous and oleophilic phases are reduced significantly from their bulk fluid values with the $T_2$ relaxation of the oleophilic phase reduced by roughly one order of magnitude and the aqueous phase reduced by about 2 orders of magnitude. The broader distribution of the aqueous phase signal may be due to solid surface effects. From FIG. 1, it can be seen that the reduction of the water relaxation time on the emulsified oil-based drilling fluid may effectively separate the aqueous and oleophilic phases on the NMR relaxation time spectrum. The valley bottom between the aqueous and oleophilic phases of the distribution on FIG. 1 is shown at reference number 8. As will be discussed in more detail below, the valley bottom may be used in determining relaxation time distribution and/or diffusivity distribution cutoffs which may be useful in determining the O/A ratio.

FIG. 1 is based on spin-spin relaxation time ($T_2$) measurements. It is expected that spin-lattice relaxation ($T_1$) should respond similarly to $T_2$ of liquids in drilling fluids. The measurement of proton self-diffusivity may add another dimension of fluid contrast, if the diffusivity of the oleophilic phase is significantly different than the aqueous phase. For example, if a viscous oil is used as the base oil for the oil-based drilling fluid, the relaxation time of the oil may be shorter than a light, non-viscous oil. This may cause the oleophilic and aqueous phase signals to partially overlap each other, while the viscous oil has a slower diffusivity than the aqueous phase. $T_1$ and $T_2$ relaxation time distributions may be obtained by a Car-Purcell-Meiboom-Gill (CPMG) distribution experiment, a saturation-recovery experiment, an inversion-recovery experiment, or any other suitable NMR technique.

A method for monitoring the oleophilic fluid to aqueous fluid ratio of a drilling fluid comprises selecting a sample of the drilling fluid that has been recirculated, measuring the NMR response of the sample of the drilling fluid and determining the oleophilic fluid to aqueous fluid ratio of the drilling fluid based at least in part on the NMR response. The oleophilic fluid to aqueous fluid ratio of the drilling fluid may be adjusted in response to the determined oil to water ratio. Drilling fluid additives may be added to the drilling fluid in response to the determined oil to water ratio. The drilling fluid additives may be any drilling fluid additive selected from the group consisting of emulsifiers, viscosifiers, density modifiers, fluid loss control additives, thinners, lost circulation materials, lubricants, corrosion inhibitors, hydrogen sulfide scavengers, salts, and combinations thereof. The drilling fluid may further comprise a paramagnetic ion selected from the group consisting of $Fe^{3+}$, $Mn^{2+}$, $Ni^{2+}$, $Cu^{2+}$, $Gd^{3+}$, 2,2,6,6,-tetramethylpiperidineyl-1-oxyl, and combinations thereof. The paramagnetic ion may be $Mn^{2+}$ and the $Mn^{2+}$ may be added to the drilling fluid as $MnCl_2$. The relaxation rate of the aqueous phase may be selectively adjusted. Selectively adjusting the relaxation rate may comprise adding a relaxation rate enhancement agent to the drilling fluid. Selectively adjusting the relaxation rate may comprise selecting particles of the drilling fluid to enhance the contrast between the oleophilic fluid and the aqueous fluid. A sample of the drilling fluid may be frozen. The NMR response of the frozen sample of the drilling fluid may be compared to an NMR response of a sample of the drilling fluid that was not frozen. The selection of the sample may comprise the sample flowing from a mud pit, solids control system, a flow line, a shaker screen, a mud pump suction inlet, a pump outlet, from within the wellbore, or from within an exit conduit of the wellbore to a fluid analysis system. The drilling fluid may be recirculated in the wellbore.

A method for monitoring the oleophilic fluid to aqueous fluid ratio of a drilling fluid comprises using an NMR spectrometer to measure the NMR response of the drilling fluid; comparing the measured NMR response to a predetermined NMR response correlated with an oleophilic fluid to aqueous fluid ratio; and selecting the oleophilic fluid to aqueous fluid ratio as the oleophilic fluid to aqueous fluid ratio of the drilling fluid. The oleophilic fluid to aqueous fluid ratio of the drilling fluid may be adjusted in response to the determined oil to water ratio. Drilling fluid additives may be added to the drilling fluid in response to the determined oil to water ratio. The drilling fluid additives may be any drilling fluid additive selected from the group consisting of emulsifiers, viscosifiers, density modifiers, fluid loss control additives, thinners, lost circulation materials, lubricants, corrosion inhibitors, hydrogen sulfide scavengers, salts, and combinations thereof. The drilling fluid may further comprise a paramagnetic ion selected from the group consisting of $Fe^{3+}$, $Mn^{2+}$, $Ni^{2+}$, $Cu^{2+}$, $Gd^{3+}$, 2,2,6,6,-tetramethylpiperidineyl-1-oxyl, and combinations thereof. The paramagnetic ion may be $Mn^{2+}$ and the $Mn^{2+}$ may be added to the drilling fluid as $MnCl_2$. The relaxation rate of the aqueous phase may be selectively adjusted. Selectively adjusting the relaxation rate may comprise adding a relaxation rate enhancement agent to the drilling fluid. Selectively adjusting the relaxation rate may comprise selecting solid particles of the drilling fluid to enhance the contrast between the oleophilic fluid and the aqueous fluid. A sample of the drilling fluid may be frozen. The NMR response of the frozen sample of the drilling fluid may be compared to an NMR response of a sample of the drilling fluid that was not frozen. The selection of the sample may comprise the sample flowing from a mud pit, solids control system, a flow line, a shaker screen, a mud pump suction inlet, a pump outlet, from within the wellbore, or from within an exit conduit of the wellbore to a fluid analysis system. The drilling fluid may be circulated in the wellbore.

A drilling fluid monitoring and handling system comprises a mud pit coupled to a fluid analysis system; and a fluid analysis system coupled to the mud pit, wherein the fluid analysis system comprises an NMR spectrometer, wherein the fluid analysis system is configured to measure and analyze the NMR response of a drilling fluid. The fluid analysis system may be configured to compute an oleophilic fluid to aqueous fluid ratio of a drilling fluid. A flow line may be disposed between the mud pit and the fluid analysis system that provides samples of the drilling fluid to the mud pit. A return line may be disposed between the mud pit and the fluid analysis system that returns samples of the drilling fluid to the mud pit. The oleophilic fluid to aqueous fluid ratio of the drilling fluid may be adjusted in response to the determined oil to water ratio. Drilling fluid additives may be added to the drilling fluid in response to the determined oil to water ratio. The drilling fluid additives may be any drilling fluid additive selected from the group consisting of emulsifiers, viscosifiers, density modifiers, fluid loss control additives, thinners, lost circulation materials, lubricants, corrosion inhibitors, hydrogen sulfide scavengers, salts, and combinations thereof. The drilling fluid may further comprise a paramagnetic ion selected from the group consisting of $Fe^{3+}$, $Mn^{2+}$, $Ni^{2+}$, $Cu^{2+}$, $Gd^{3+}$, 2,2,6,6,-tetramethylpiperi-dineyl-1-oxyl, and combinations thereof. The paramagnetic ion may be $Mn^{2+}$ and the $Mn^{2+}$ may be added to the drilling fluid as $MnCl_2$. The relaxation rate of the aqueous phase may be selectively adjusted. Selectively adjusting the relaxtion rate may comprise adding a relaxation rate enhancement agent to the drilling fluid. Selectively adjusting the relaxation rate may comprise selecting solid particles of the drilling fluid to enhance the contrast between the oleophilic fluid and the aqueous fluid. A sample of the drilling fluid may be frozen. The NMR response of the frozen sample of the drilling fluid may be compared to an NMR response of a sample of the drilling fluid that was not frozen. The selection of the sample may comprise the sample flowing from a mud pit, solids control system, a flow line, a shaker screen, a mud pump suction inlet, a pump outlet, from within the wellbore, or from within an exit conduit of the wellbore to a fluid analysis system. The drilling fluid may be circulated in the wellbore.

Figure 2:
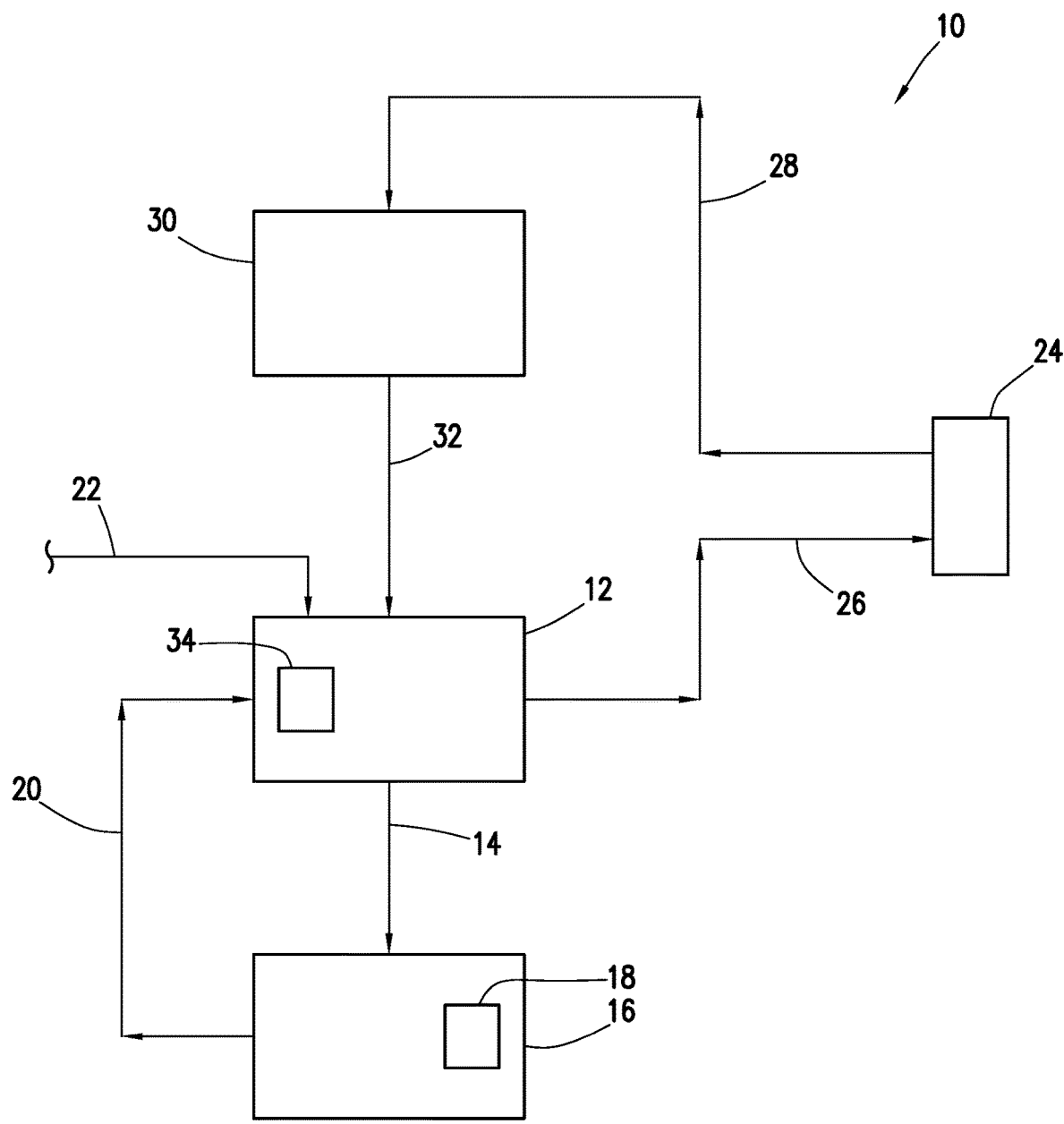
FIG. 2 illustrates an example block diagram using a fluid handling and monitoring system.

Referring now to FIG. 2, a block flow diagram is shown generally depicting an overview of the drilling fluid monitoring and handling system 10 for monitoring properties of drilling fluids such as the O/A ratio. As illustrated, a sample of the drilling fluid from mud pit 12 may be pumped via mud pit line 14 to a fluid analysis system 16. Alternatively, the sample may be conditioned in a fluid supply system (not shown), which may comprise a pump and filtering equipment to remove solids such as calcium carbonate and/or lost circulation materials. Fluid analysis system 16 may comprise an NMR spectrometer 18 capable of measuring the NMR response of the sample of the drilling fluid to determine the O/A ratio. After fluid analysis, the sample of the drilling fluid may be returned to mud pit 12 via return line 20 or, alternatively, the sample may be disposed of. The drilling fluid within mud pit 12 may be altered, for example, by the addition of oleophilic fluid and/or aqueous fluid to adjust the O/A ratio of the drilling fluid based at least in part on the analysis provided by the NMR spectrometer 18 within the fluid analysis system 16. Analogously, drilling fluid additives via a drilling fluid additive supply 22 may be added to mud pit 12 consistent with the analysis provided by the fluid analysis system 16. After the drilling fluid has been adjusted, another sample of the drilling fluid may be retested to verify the drilling fluid was correctly formulated by transferring the drilling fluid to fluid analysis system 16 via mud pit line 14 or the drilling fluid may be sent to the wellbore 24 for use in drilling fluid operations via wellbore supply line 26.

In alternative embodiments, a sample of circulated drilling fluid from wellbore return line 28 may be removed from solids control system 30. Solids control system 30 may feed circulated drilling fluid to mud pit 12 via solids control line 32. The circulated drilling fluid may be treated by the solids control system 30 prior to a sample being removed, or alternatively, a sample may be removed prior to treatment by solids control system 30 if desired. The sample may be measured by the NMR spectrometer 18 in the fluid analysis system 16. The sample may be pumped or otherwise moved to the fluid analysis system 16 via a flowline, conduit, or any suitable transport method (not shown).

The drilling fluid may be any oil based drilling fluid ("OBM"), including emulsified oil-based drilling fluids. An emulsified oil based drilling fluid is a drilling fluid in which the continuous phase is an oleophilic fluid and the internal phase is an aqueous fluid. Examples of oleophilic fluids may include hydrocarbon liquids or more generally any product obtained from oil such as diesel oil or mineral oil. Further, the term oleophilic fluid also encompasses synthetic muds or any nonaqueous fluid that is analogous to oil muds and may be analyzed using the methods and systems described herein, e.g., paraffins, olefins, esters, and the like. The O/A ratio describes the ratio of the oleophilic fluid to the aqueous fluid. The drilling fluid may additionally comprise drilling fluid additives, which may include viscosifiers, emulsifiers, density modifiers, etc. The drilling fluid may comprise solids. The solids may be any type of solids found in a wellbore or introduced into a wellbore fluid. Without limitation, examples of solids may include pieces of the formation, drill cuttings, and additives introduced to a drilling fluid, e.g., lost circulation materials, etc. The solids may be of any of a variety of sizes and shapes. The drilling fluid may be analyzed as described herein to determine one or more fluid properties. For example, the drilling fluid may be analyzed to determine the O/A ratio.

Mud pit 12 may be any vessel suitable for holding a drilling fluid. Drilling fluid additives may be added to mud pit 12 if desired. Mud pit 12 may comprise a container such as a drum or tank, or a series of containers that may or may not be connected. Mud pit 12 may comprise mixing equipment to mix the contents of mud pit 12 as well as any drilling fluid additives. Mud pit 12 may further comprise pumping equipment to pump the contents of mud pit 12, for example, to pump a drilling fluid to fluid supply system 16 via mud pit line 14 or to pump a drilling fluid to the wellbore via wellbore supply line 26.

As noted above, mud pit 12 may comprise a mixing system, illustrated in FIG. 2 as mixing system 34. Mixing system 34 may use any suitable mixing technique for mixing of the drilling fluid. While not illustrated, in the disclosed examples, mixing system 34 may also mix emulsifiers, viscosifiers, density modifying agents, and other drilling fluid additives with the drilling fluid. Further, should the O/A ratio require adjustment based on the analysis provided by NMR spectrometer 18, additional oleophilic fluid or aqueous fluid may be added to the drilling fluid in mud pit 12 and mixed by mixing system 34. Finally, mixing system 34 may more generally be used to prevent the settling of solids if desired. Mixing system 34 may use any of a variety of different mixing equipment, such as static or dynamic mixers. One example of suitable mixing equipment may comprise a vessel with a paddle wherein the paddle may be used to mixing the drilling fluid.

Fluid analysis system 16 may comprise an NMR spectrometer 18. Fluid analysis system 16 may use at least one NMR spectrometer 18 to analyze a drilling fluid to determine the O/A ratio. Additionally, fluid analysis system 16 may measure other fluid properties using additional measurement devices and/or techniques such as optical measuring systems, imaging measuring systems, laser measuring systems, ultrasound measuring systems, pH measuring systems, and titration systems, among others. Combinations of fluid analysis techniques may also be used.

The NMR spectrometer may be any type of NMR spectrometer useful for measuring the NMR response of a drilling fluid. The field strength medium may be a medium to low field, (e.g., a 1-50 MHz system). High field systems may be used in certain applications. Without limitation, the NMR spectrometer may measure the NMR response of any nuclei of interest including $^1H$, $^{31}P$, $^{19}F$, and other sensitive nuclei. The NMR spectrometer may use any radio frequency necessary to generate an NMR response in corresponding nuclei. Optionally, the NMR may require calibration before calculating the NMR response of a specific sample. Further, a lookup table may be prepared in advance of or after sample measurement if desired. The lookup table may be used to determine the amount of adjustment necessary, if any, to obtain a desirable O/A ratio for a drilling fluid after measurement of the NMR response of the drilling fluid. A "lookup table," as used herein, may include any array, database, matrix, or other similar arrangement usable to cross reference data (e.g., one or more numerical values, parameters, attributes, factors, properties, etc.). Generally speaking, a lookup table may relate the values of one or more input characters to a corresponding output value. In some examples, a two-dimensional lookup table may be employed for input parameters such as type of nuclei measured, standard used (e.g., tetramethylsilane), chemical shift value, type of drilling fluid the sample was isolated from, presence of additives/solids and the like, known O/A ratio of base fluid, viscosity of the drilling fluid, etc.; the two-dimensional lookup table may relate particular values of any of parameters to a corresponding amount of for at least one component and/or property of the drilling fluid, such that when specific values of the input parameters are input to the lookup table, the lookup table may produce a corresponding amount of adjustment for a component and/or property of the drilling fluid that may result in a drilling fluid comprising the desired O/A ratio. Further, this may also provide a more complete model of downhole conditions.

Solids control system 30 may be used to condition the drilling fluid prior to returning the drilling fluid to mud pit 12. Such processes may include, but are not limited to, a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The solids control system 30 may further include one or more sensors, gauges, pumps, compressors, and the like used store, monitor, regulate, and/or recondition the drilling fluid and various additives thereto.

Figure 3:
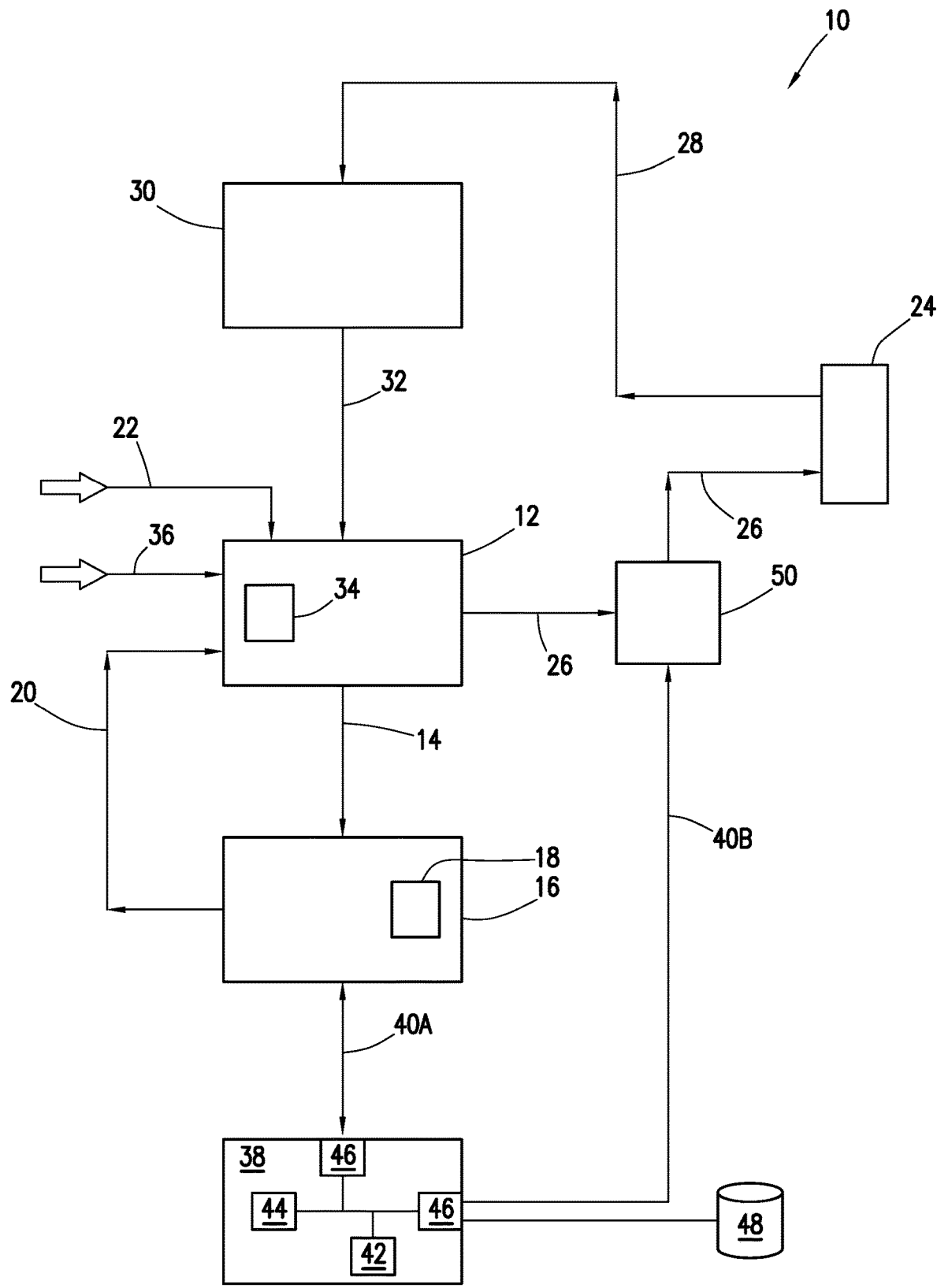
FIG. 3 illustrates an example drilling fluid handling and monitoring system using an NMR spectrometer to analyze the NMR response of a drilling fluid during a drilling operation.

Referring now to FIG. 3, an example of the fluid monitoring and handling system 10 is shown in more detail. As illustrated, the fluid monitoring and handling system 10 may comprise mud pit 12, fluid analysis system 16, solids control system 30, and additional components/systems. Mud pit 12 may be supplied with a drilling fluid from an initial drilling fluid supply line 36, return line 20, solids control system 30, etc. Drilling fluid supply line 36 provides an initial supply of drilling fluid to mud pit 12. The initial supply of drilling fluid does not imply that the drilling fluid has not been recycled or circulated in the wellbore at some point in the life cycle of the drilling fluid, but simply indicates that this supply is not presently being circulated or otherwise used in the wellbore. A mud-mixing hopper (not shown) may be coupled to initial drilling fluid supply line 36 and used to mix a new or reused drilling fluid before the drilling fluid is sent to the mud pit 12. Return line 22 may returns sample of drilling fluid used in the fluid analysis system 16 to mud pit 12. As discussed above, mud pit 12 may comprise mixing system 34 which may be used to mix a drilling fluid with drilling fluid from initial drilling fluid supply line 36, return line 22, and/or solids control system 30, as well as with any drilling fluid additives, additional oleophilic fluid, and/or aqueous fluid. Additionally, mixing system 34 may be used to prevent solids within the drilling fluid from settling. Mixing system 34 may comprise a static mixer, dynamic mixer, of other suitable mixer.

As described above, mud pit line 14 may convey a portion of the drilling fluid to the fluid analysis system 16 where a sample portion of the drilling fluid may analyzed by NMR spectrometer 18. Mud pit line 14 may be a suction line, and as such would pull the portion of the drilling fluid from mud pit 12 to fluid analysis system 16. Additionally, a fluid supply system (not shown) may be used to condition the drilling fluid, for example, by removing solids such as calcium carbonate or lost circulation additives. The fluid supply system may comprise at least one fluid supply pumping system which comprises a pump and associated conduits. The pump may be any type of pump suitable for pumping the portion of the drilling fluid to the fluid analysis system 16 including a mud pump or analogous pump and/or pumping system.

Fluid analysis system 20 may analyze the NMR response of the sample of the drilling fluid. As described above, fluid analysis system 16 may comprise an NMR spectrometer 18. Optionally, NMR spectrometer 18 may analyze the sample of the drilling fluid at a standard laboratory pressure and temperature (e.g., 1 atm, 25° C.) to provide consistent measurements. Using the NMR spectrometer 18 as described above, the fluid analysis system 16 may measure the NMR response of the sample of the drilling fluid and record the results. In some examples, the NMR response may comprise the chemical shift of the component molecules within the drilling fluid relative to a standard. A standard may be any such standard desired for use, examples of which include tetramethylsilane. The NMR response measurement, recordation, and analysis process may be automated in part or in whole. Alternatively, the process may not be automated. Further the process may provide feedback for the adjustment of one or more components of the fluid monitoring and handling system 10. For example, the results of the analysis performed by the fluid analysis system 20 may indicate that adjustment should be made at an upstream or downstream process within or external to the fluid monitoring and handling system 10 as discussed below. Such adjustment may be automated in part or in whole. Alternatively, said adjustment may not be automated. Further alternatively, such adjustment may not be made if desired.

The measurement made by the NMR spectrometer 18 may comprise using the NMR spectrometer 18 to measure the NMR response of the sample of the drilling fluid. Without limitation, the NMR spectrometer may measure the NMR response of any nuclei of interest including $^1H$, $^{31}P$, $^{19}F$, and the like. The NMR spectrometer may use any radio frequency necessary to generate an NMR response in corresponding nuclei. Optionally, the NMR may require calibration before calculating the NMR response of a specific sample. The NMR may be used to measure the relaxation times and diffusivities of a sample of the drilling fluid. The relaxation times and diffusivities of the sample of drilling fluid may be used to quantitatively determine the O/A ratio of the sample of the drilling fluid. The NMR spectrometer 18 may be in-line with other components/systems within the fluid monitoring and handling system 10.

As discussed above, optional calibration steps may be used. The calibration steps may be done for, amongst other reasons, to determine the hydrogen index correction. Calibration may comprise using the NMR spectrometer 18 (or other suitable NMR spectrometer) to measure the relaxation time distribution and/or diffusivity distribution and additionally the hydrogen index of the base oleophilic fluid at a given temperature. The NMR spectrometer 18 (or other suitable NMR spectrometer) may be used to measure the whole oleophilic phase, which may include every component of the oleophilic phase, such as oil-miscible additives, oil-dissolved additives, etc. in order to determine the relaxation time distribution and/or diffusivity distribution and additionally the hydrogen index of the whole oleophilic phase at a given temperature. The NMR spectrometer 18 may be used to measure the base aqueous fluid to determine the hydrogen index of the base aqueous fluid at a given temperature. Then the NMR may be used to measure the whole drilling fluid comprising a known O/A ratio for the oleophilic phase and the aqueous phase to determine the cutoff relaxation times which may separate the oleophilic phase signal from the aqueous phase signal. This step may be repeated as desired by varying the known O/A ratio for the oleophilic phase and the aqueous phase. Further, the process may be repeated for different types as desired by varying the volumetric ratio of any additives, solids, etc. The disclosed process may be used to generate data which may be incorporated into a lookup table as described above. The calibration data obtained may be used to interpolate the relaxation time cutoff value as a function of the O/A ratio and also the solid/liquid ratio.

When measuring a sample of drilling fluid with the NMR spectrometer 18 in which the O/A is not known, the same relaxation time and/or diffusivity measurement techniques used in the calibration process described above may be used and a data inversion technique may then be applied to obtain the relaxation time distribution and/or diffusivity distribution of the unknown mud. The relaxation time distribution may be considered as $P_i(T_{1,i})$ wherein i=1 to $i_{max}$, wherein $i_{max}$ represents the numbers of bins to represent the relaxation time distribution of the unknown mud. The diffusivity distribution may be considered as $Q_j(T_{1,j})$ wherein j=1 to $j_{max}$, wherein $j_{max}$ represents the numbers of bins to represent the diffusivity time distribution of the unknown mud.

In order to determine the relaxation time and/or diffusivity cutoff, the valley bottom of the distribution may need to be determined. The valley bottom of the distribution generally may separate the oleophilic signal from the water signal on the relaxation time distribution and/or diffusivity distribution. The valley bottom may generally correspond to the valley separating the peaks on the relaxation time distribution and/or diffusivity distribution. The relaxation time that corresponds with the approximate center of the valley bottom may be referred to as $T_{2K}$.

The NMR signal amplitudes of the oleophilic phase fluid and aqueous phase fluid may then be determined by integrating the relaxation time and/or diffusivity spectrum by calculating the total fluid signal via equation 1:

$$SP_{oleophilic+aqueous} = \Sigma_1^{imax} P_i \qquad \text{(Eq. 1)}$$

Where $SP_{oleophilic+aqueous}$ is the total fluid signal, P is fluid signal at i, i is an integer, and $i_{max}$ is the total number of bins to represent the relaxation time distribution for the unknown mud. The fluid signal of the oleophilic phase may be measured by equation 2:

$$SP_{oleophilic} = P_K/2 + \Sigma_{K+1}^{imax} P_i \qquad \text{(Eq. 2)}$$

Where $SP_{oleophilic}$ is the fluid signal of the oleophilic phase, K is the bin representing the cutoff, $P_K$ is signal at the cutoff, i is an integer, and $i_{max}$ is the total number of bins to represent the relaxation time distribution for the unknown mud. The aqueous phase fluid signal may then be measured by equation 3:

$$SP_{aqueous} = \Sigma_1^{imax} P_i - SP_{oleophilic} \qquad \text{(Eq. 3)}$$

Where $SP_{aqueous}$ is the fluid signal of the aqueous phase, P is fluid signal at i, i is an integer, and $i_{max}$ is the total number of bins to represent the relaxation time distribution for the unknown mud, and $SP_{oleophilic}$ is the fluid signal of the oleophilic phase. Finally, the hydrogen index (HI) obtained from the calibration process may be used to give the volumetric ratio of oleophilic phase and the aqueous phase using equations 4 and 5:

$$V_{oleophilic} = \frac{SP_{oleophilic}}{HI_{oleophilic}} \qquad \text{(Eq. 4)}$$

Where $V_{oleophilic}$ is the uncalibrated oleophilic volume, $SP_{oleophilic}$ is the fluid signal of the oleophilic phase, and $HI_{oleophilic}$ is the hydrogen index for the oleophilic phase. The $HI_{oleophilic}$ may correspond to the hydrogen index correction for the particular relaxation time and/or diffusivity cutoff. $HI_{oleophilic}$ may be 1 or less than 1.

$$V_{aqueous} = \frac{SP_{aqueous}}{HI_{aqueous}} \qquad \text{(Eq. 5)}$$

Where $V_{aqueous}$ is the uncalibrated aqueous volume, $SP_{aqueous}$ is the fluid signal of the aqueous phase, and $HI_{aqueous}$ is the hydrogen index for the aqueous phase. The $HI_{aqueous}$ may be used in the hydrogen index correction for the particular relation time and/or diffusivity cutoff.

Further, if using a lookup table, the $T_{2K}$ value of the unknown mud, discussed above, may be compared with the corresponding value in the lookup table for the O/A ratio and/or the solid/liquid ratio measurements of the unknown mud to see if the two are consistent with each other within a desired tolerance range. This optional and additional step may be used in any quality control analysis of the process.

In some examples, the NMR responses of the oleophilic and aqueous phases may not have a sufficient enough contrast so as to be distinguishable. This may be because there is overlap in the relaxation time distribution or the diffusivity distribution. This may result in an uncertainty in determining the O/A ratio. In such examples, a number of different techniques may be used to selectively adjust the relaxation rate of either the oleophilic or aqueous phases.

Typically, drilling fluids may contain a substantial volume fraction of fine-sized solid particles, such as sand, barite, and/or silt. The fluid molecules may interact with the molecules on the surface areas of the solids particles, which effectively reduces the relaxation time of the proton in the fluids, provided that the time required to have diffusional exchange between the proton near and far away from the solid surfaces is shorter than the characteristic time of NMR measurements. Accordingly, it may be expected that the measured relaxation rate of the fluid is the collective effective of the bulk relaxation rate plus the surface relaxation rate:

$$\frac{1}{T_{2\ measured}} = \frac{1}{T_{2\ bulk}} + \rho \frac{A}{V} \qquad (Eq.\ 6)$$

Where $T_{2\ measured}$ is the measured relaxation rate of the fluid, $T_{2\ bulk}$ is the bulk relaxation rate, $\rho$ is the surface relaxivity, A is the total surface area, and V is the fluid volume. As can be seen in equation (6), the longer the bulk relaxation time, the more dominant the second $$\left(\rho \frac{A}{V}\right)$$

in determining the relaxation rate of the fluid. The larger the surface relaxivity ($\rho$), the more it effectively reduces the fluid's relaxation time. The stronger intermolecular forces between the wetting fluid phase molecules and the surface results in a significantly larger surface relaxivity ($\rho$), in comparison to the non-wetting fluid phase. Since the aqueous phase is typically the wetting phase with the solids in an emulsified oil-based drilling fluid, the corresponding $\rho_{aq}$ is expected to be significantly larger than that corresponding to the non-wetting or weakly wetting oleophilic phase, $\rho_{ol}$. Thus, the aqueous phase fluid relaxation time is expected to be shorter than that of the oleophilic phase in these emulsified oil-based drilling fluids.

However, when the signals of these two fluid phases partially overlap in the $T_1$ or $T_2$ distribution, it is likely that the oleophilic phase may have faster relaxation components. In order to separate the signals, it may be more practical to increase the relaxation rate of the aqueous phase instead of the relaxation rate of the oleophilic phase. From equation 5, it can be seen that increasing the relaxation rate of the aqueous phase may be achieved by either enhancing the surface relaxivity of the aqueous phase ($\rho_{aq}$) or increasing the surface area (A).

One technique to selectively adjust the relaxation rate of the aqueous phase may include designing the solid particles of the drilling fluid to enhance the contrast between the oleophilic and aqueous phases. This can be done by selecting solid particles that either have a large surface relaxivity ($\rho_{aq}$) or reducing the particle size to increase surface area (A), or both. When selecting particles, it may be desired that the desired drilling fluid performance is not degraded by the selection. In general, minerals having paramagnetic and/or ferromagnetic ions may lead to a much stronger surface relaxivity ($\rho$), wherein certain clay species may be selected. It may be desired to selected solid particles to be as small as possible without inadvertently affecting drilling fluid performance. For the same solid particle volume, the size of the solid particles may be decreased to increase the surface area by a facto proportional to the particle size. Clay particles may be selected that have a large surface area/volume ratio for the same volume of fluids.

Another technique to selectively adjust the relaxation rate of the aqueous phase may include addition of a relaxation rate enhancement agent. These additives may be included in the drilling fluid when originally formulated, added via drilling fluid additive supply line 24, or added directly to the sample of the drilling fluid before measurement by the NMR spectrometer 18 in the fluid analysis system 16. Where the relaxation rate enhancement agent may be used, equation (6) above may be modified as follows:

$$\frac{1}{T_{2\ measured}} = \frac{1}{T_{2\ bulk}} + \rho \frac{A}{V} + \frac{1}{T_{2\ PRE}} \qquad (Eq.\ 6)$$

Where $T_{2\ PRE}$ is the relaxation rate of the relaxation rate enhancement agent. When the effect of the third term is proportionally large, the total relaxation rate of the fluid may be proportional to the concentration of the relaxation rate enhancement agent.

The relaxation rate enhancement agents may be added in any suitable amount, for example, in an amount in a range of about $10^0$ to about $10^3$ ppm. The amount of the relaxation rate enhancement agents may be selected so as to not interfere with fluid/solid ratio in any discernible manner. As the relaxation rate may be proportional to agent concentration, the concentration of the relaxation rate enhancement agent maybe controlled to generate the desired enhancement of the relaxation rate. It may desirable for the relaxation rate enhancement agents to be stable in a suspension and to be soluble in the aqueous phase, but not the oleophilic phase (or vice versa). Additionally, it may be desirable that the relaxation rate enhancement agents not form bonds with other solids so as to not dilute or deteriorate the effectiveness of the relaxation rate enhancement agents. Examples of relaxation rate enhancement agents may include, but are not limited to, paramagnetic ion species comprising $Fe^{3+}$, $Mn^{2+}$, $Ni^{2+}$, $Cu^{2+}$, $Gd^{3+}$, 2,2,6,6,-tetramethylpiperidineyl-1-oxyl (also called "TEMPO") ions, and mixtures thereof. The paramagnetic ion species may come from sources such as salts, oxides, nitrates, etc. Examples of paramagnetic ion sources include, but are not limited to $MnCl_2$, $Fe(NO_3)_3$, $MnO_2$, $NiSO_4$, $CuSO_4$, and the like. Further it may be desirable to use relaxation rate enhancement agents that do not interact with the formation if the relaxation rate enhancement agents are to be pumped with the drilling fluid into the formation. Additionally, in some examples chelating the paramagnetic species may be desirable to prevent the relaxation rate enhancement agents from exchanging with metal ions which may be present in some of the oleophilic fluids. An example of a chelated relaxation rate enhancement agent is $Mn^{2-}$-EDTA. If the drilling fluid is emulsified, it may be necessary to demulsify the fluid so as to allow the relaxation rate enhancement agents to make ready contact with the aqueous phase of the drilling fluid. The relaxation rate enhancement agents may add contrast to either the aqueous of oleophilic phase of the drilling fluid and enhance the chemical shift contrast between the two, allowing for a more accurate determination of the O/A ratio of a drilling fluid.

In further examples where the oleophilic phase and the aqueous phase comprise overlapping chemical shifts, a sample of drilling fluid with a relaxation rate enhancement agent may be prepared and compared with a sample of drilling fluid without a relaxation rate enhancement agent. Separate, identical relaxation time measurements may be conducted by NMR spectrometer 18 on each sample. By comparing the two peak shifts for the relaxation time distributions, the effect of the relaxation rate enhancement agent on one of the fluid phases (e.g., the aqueous phase) may be determined. Thus, the comparison may allow one having ordinary skill in the art to not the contrast between the NMR signal amplitudes of the oleophilic and aqueous phases, and this determine the O/A ratio of the drilling fluid.

In still further examples where the oleophilic phase and the aqueous phase may comprise overlapping relaxation distributions and yet also comprise distinctive freezing points, one of the fluid phases may be selectively frozen. The frozen, or solid phase, should not be sensed by a relaxation time measurement with a finite interecho time CPMG measurement, leaving only the NMR response of the unfrozen phase to be detected. Thus, the NMR response of the selectively frozen sample of drilling fluid may then be compared with the NMR response of a completely unfrozen sample of drilling fluid to isolate which peak(s) in the completely unfrozen sample is the one represented by the unfrozen fluid portion of the selectively frozen sample. Once said peak(s) are known, the O/A ratio of the sample of drilling fluid may be determined.

The examples disclosed herein contemplate the removal of a sample of drilling fluid at any desirable point in the fluid monitoring and handling system 10. For example, a sample of the drilling fluid may be removed from the mud pit 12, from the solids control system 30, from a flow line, from a shaker screen, from a mud pump suction inlet, from a pump outlet, from within the wellbore, or from within an exit conduit of the wellbore. As such, all examples disclosed herein contemplate the measuring of the NMR response at any point in the drilling fluid handling process, so that the drilling fluid may be monitored and/or subsequently adjusted as desired.

With continued reference to FIG. 3, the analysis undertaken by the fluid analysis system 16 may be performed by computer system 38. Computer system 38 may be an internal or external component of fluid analysis system 16. FIG. 3 illustrates computer system 38 as an external component of fluid analysis system 16. Computer system 38 may be connected to fluid analysis system 16 via communication link 40A. Communication link 40A may include a direct connection, a private network, a virtual private network, a local area network, a WAN (e.g., an Internet-based communication system), a wireless communication system (e.g., a satellite communication system, telephones), combinations thereof, or any other suitable communication link. Computer system 38 may be any suitable data processing system, including computer systems, handheld devices, or any other suitable device. A suitable data processing system may include processor 42, memory 44, and software operable on processor 42 to process and analyze the measurement data generated by fluid analysis system 16, adjust the parameters of fluid monitoring and handling system 10, and/or operate a part or the whole of fluid monitoring and handling system 10. Computer system 38 may further comprise input/output ("I/O") interface(s) 46. Processor 42 may comprise one central processing unit or may be distributed across one or more processors in one or more locations. Memory 44 should be communicatively coupled to processor 42. Memory 44 may be read-only memory, random-access memory, or the like. I/O interface(s) 46 should be communicatively coupled to processor 42. I/O interface(s) 46 may be any suitable system for connecting computer system 38 to a communication link, such as a direct connection, a private network, a virtual private network, a local area network, a wide area network ("WAN"), a wireless communication system, or combinations thereof; storage devices, such as storage 48; external devices, such as a keyboard, a monitor, a printer, a voice recognition device, or a mouse; or any other suitable system. Optionally, storage 48 may also be provided. Storage 48 may be communicatively coupled to I/O interface(s) 46 or to processor 42. Storage 48 may comprise any device suitable for storing data to be processed, including, but not limited to, compact disc drives, floppy drives, hard disks, flash memory, solid state drives, and the like. Those of ordinary skill in the art will appreciate that suitable data processing systems may comprise additional, fewer, and/or different components than those described for computer system 38.

Data processing and analysis software native to fluid analysis system 16 and/or installed on computer system 38 may be used to analyze the data generated by fluid NMR spectrometer 18 within a fluid analysis system 16. This procedure may be automated such that the analysis happens without the need for operator input or control. Further, the operator may select from several previously input parameters or may be able to recall previously measured data. Any of the data may be transferable and/or storable on a USB drive if desired.

Return line 20 may return the sample of the drilling fluid to mud pit 12 from fluid analysis system 16. Alternatively, the sample may be disposed of. Drilling fluid additives may be added to mud pit 12 via drilling fluid additive supply line 22 based on the analysis of fluid analysis system 16. Should the drilling fluid require further analysis it may be further analyzed. Alternatively, portions of the drilling fluid may be continuously analyzed and returned to mud pit 12 in a continuous process with drilling fluid additives and/or aqueous fluid or oleophilic fluid added to maintain a strong and stable drilling fluid. Similarly, measurements made within the wellbore may provide information as to formation features (e.g., a salt stream) that the drilling fluid may interact with as a drilling operation continues. If said information is known, the drilling fluid may be formulated to anticipate said formation features. Fluid analysis system 16 may be used to validate that the correct anticipatory formulation has been achieved prior to pumping the drilling fluid into the wellbore and the aforementioned subject formation feature.

With continued reference to FIG. 3, if a drilling fluid is of a satisfactory formulation, the drilling fluid may be pumped via wellbore supply line 26, which may be a suction line, to mud pump 50 which may pump the drilling fluid into the wellbore 24. Mud pump 50 may be any type of pump or pumping system useful for circulating a drilling fluid into a subterranean formation under a sufficient pressure. Drilling fluid that has been circulated within the wellbore 24, may be returned to mud pit 12 via wellbore return line 28. Solids control system 30 may be used to condition the drilling fluid prior to returning the drilling fluid to mud pit 12. Such processes may include, but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. Solids control system 30 may further include one or more sensors, gauges, pumps, compressors, and the like used store, monitor, regulate, and/or recondition the drilling fluid and various additives thereto. After the drilling fluid has been reconditioned, the drilling fluid may be returned to mud pit 12 via solids control line 32. Communication link 40B may link solids control system 30 to computer system 38. Communication link 40B may include a direct connection, a private network, a virtual private network, a local area network, a WAN (e.g., an Internet-based communication system), a wireless communication system (e.g., a satellite communication system, telephones), combinations thereof, or any other suitable communication link. Communication link 40B may allow computer system 38 to adjust the parameters of solids control system 30 based on the measurement of the NMR response by fluid analysis system 20. Further, fluid analysis system 16 may be used to adjust the amount of and type of additives used and supplied via drilling fluid additive supply 22. This process may be conducted via a separate communication link with the vessel or vessels in which the drilling fluid additives may be stored (not shown). Additionally, fluid analysis system 16 may be used to adjust the ratio of oleophilic fluid to aqueous fluid in any such drilling fluid supplied via initial drilling fluid supply line 36 should a new or uncirculated supply of drilling fluid be required.

Figure 4:
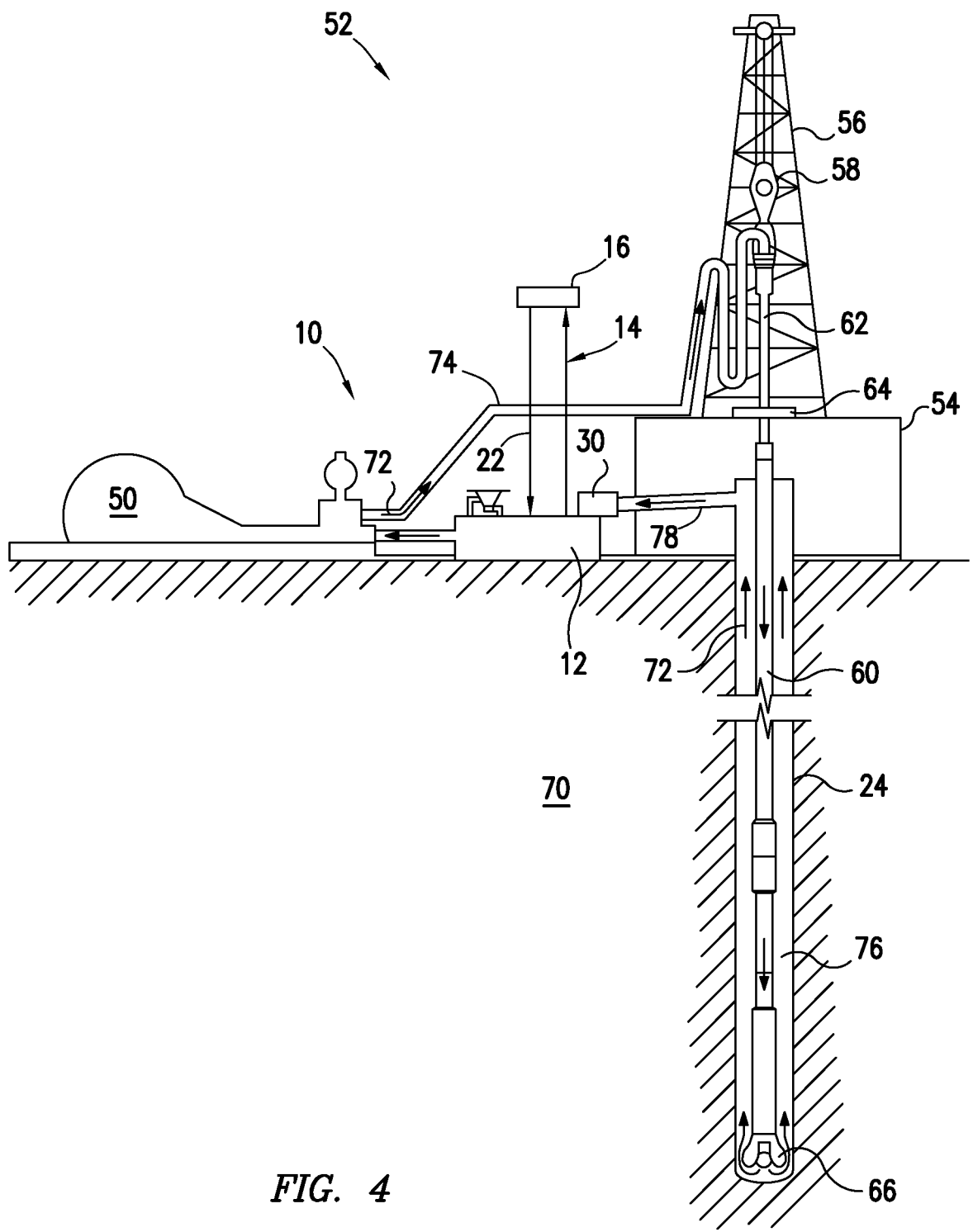
FIG. 4 illustrates an example drilling fluid system using a drilling fluid handling and monitoring system.

Referring now to FIG. 4, the disclosed fluid monitoring and handling system 10 may be used in conjunction with a drilling system 52. It should be noted that while FIG. 4 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 52 may include a drilling platform 54 that supports a derrick 56 having a traveling block 58 for raising and lowering a drill string 60. The drill string 60 may include, but is not limited to, drill pipe and coiled tubing, as generally known to those skilled in the art. A kelly 62 may support the drill string 60 as it may be lowered through a rotary table 64. A drill bit 66 may be attached to the distal end of the drill string 60 and may be driven either by a downhole motor and/or via rotation of the drill string 60 from the well surface. Without limitation, the drill bit 66 may include, roller cone bits, PDC bits, natural diamond bits, any hole openers, reamers, coring bits, and the like. As the drill bit 66 rotates, it may create a wellbore 24 that penetrates various subterranean formations 70.

The drilling system 52 may further include a fluid monitoring and handling system 10 comprising component parts such as mud pump 50, one or more solids control systems 30, and a mud pit 12. The mud pump 50 representatively includes any conduits, pipelines, trucks, tubulars, and/or pipes used to fluidically convey the drilling fluid 72 downhole, any pumps, compressors, or motors (e.g., topside or downhole) used to drive the drilling fluid 72 into motion, any valves or related joints used to regulate the pressure or flow rate of the drilling fluid 72, and any sensors (e.g., pressure, temperature, flow rate, etc.), gauges, and/or combinations thereof, and the like.

The mud pump 50 may circulate drilling fluid 72 through a feed pipe 74 and to the kelly 62, which may convey the drilling fluid 72 downhole through the interior of the drill string 60 and through one or more orifices in the drill bit 66. The drilling fluid 72 may then be circulated back to the surface via an annulus 76 defined between the drill string 60 and the walls of the borehole 68. At the surface, the recirculated or spend drilling fluid 72 may be conveyed to the fluid reconditioning system 50 via an interconnecting flow line 78. After passing through the solids control system 30, a "cleaned" drilling fluid 72 may be deposited into a nearby mud pit 12. While illustrated as being arranged at the outlet of the wellbore 24 via the annulus 76, those skilled in the art will readily appreciate that the solids control system 30 may be arranged at any other location in the drilling system 52 to facilitate its proper function, without departing from the scope of the scope of the disclosure.

Referring still to FIG. 4, the fluid monitoring and handling system 10 may further include a fluid analysis system 16, which may be disposed on a skid supported on the platform 54. The fluid analysis system 16 may, for example, may measure the NMR response of a sample of drilling fluid 72. As illustrated, a sample of drilling fluid 72 may be taken from the mud pit 12 via a mud pit line 14, and optionally, the analyzed sample of drilling fluid 72 may be returned to the mud pit 12 via return line 20. Alternatively, the NMR response of a sample of the drilling fluid may be measured, recorded, and/or analyzed at solids control system 30 or even while in the wellbore 24 if desired.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method for monitoring an oleophilic fluid to aqueous fluid ratio of a drilling fluid comprising:
    sending a sample of the drilling fluid that has been recirculated out of a wellbore to a fluid analysis system, wherein the sample of the drilling fluid comprises an oleophilic phase and an aqueous phase;
    selectively adjusting a relaxation rate of the aqueous phase;
    measuring a nuclear magnetic resonance (NMR) response of the sample of the drilling fluid in the fluid analysis system;
    determining the oleophilic fluid to an aqueous fluid ratio of the drilling fluid based at least in part on the NMR response of the sample of the drilling fluid and determining a valley bottom of a distribution of the NMR response of the drilling fluid, wherein the distribution is a relaxation time distribution, and wherein the valley bottom separates an oleophilic signal from a water signal on the relaxation time distribution;
    returning the sample of the drilling fluid used in the fluid analysis system to the drilling fluid; and
    adjusting an amount of one or more drilling fluid additives in the drilling fluid based in part to the oleophilic fluid to aqueous fluid ratio before introducing into the wellbore.

2. A method according to claim 1, further comprising adjusting the oleophilic fluid to aqueous fluid ratio of the drilling fluid in response to the oleophilic to aqueous fluid ratio.

3. A method according to claim 1, wherein the drilling fluid additives may be any drilling fluid additive selected from the group consisting of emulsifiers, viscosifiers, density modifiers, fluid loss control additives, thinners, lost circulation materials, lubricants, corrosion inhibitors, hydrogen sulfide scavengers, salts, and combinations thereof.

4. A method according to claim 1, wherein the drilling fluid further comprises a paramagnetic ion selected from the group consisting of $Fe^{3+}$, $Mn^{2+}$, $Ni^{2+}$, $Cu^{2+}$, $Gd^{3+}$, 2,2,6,6,-tetramethylpiperidineyl-1-oxyl, and combinations thereof.

5. A method according to claim 4, wherein the paramagnetic ion is $Mn^{2+}$ and further wherein the $Mn^{2+}$ is added to the drilling fluid as $MnCl_2$.

6. A method according to claim 1, wherein the selectively adjusting comprises adding a relaxation rate enhancement agent to the drilling fluid.

7. A method according to claim 1, wherein the selectively adjusting comprises selecting solid particles of the drilling fluid to enhance a contrast between the oleophilic fluid and the aqueous fluid.

8. A method according to claim 1, further comprising freezing the sample of the drilling fluid to form a frozen sample and comparing the NMR response of the frozen sample of the drilling fluid to an NMR response of a liquid sample of the drilling fluid.

9. A method according to claim 1, wherein the sending the sample comprises the sample flowing from a mud pit, solids control system, a flow line, a shaker screen, a mud pump suction inlet, a pump outlet, from within the well bore, or from within an exit conduit of the well bore.

10. A method according to claim 1, wherein the step of determining the oleophilic fluid to aqueous fluid ratio comprises interpolating a relaxation time cutoff value as a function of ratio of the oleophilic phase to the aqueous phase.

11. A method for monitoring an oleophilic fluid to aqueous fluid ratio of a drilling fluid comprising:
    providing a sample of the drilling fluid that has been recirculated out of a wellbore from a mud pit to a fluid analysis system, wherein the drilling fluid comprises an oleophilic phase and an aqueous phase and selectively adjusting a relaxation rate of the aqueous phase;
    using a nuclear magnetic resonance (NMR) spectrometer in the fluid analysis system to measure an NMR response of the drilling fluid;
    comparing the measured NMR response to a predetermined NMR response correlated with an oleophilic fluid to aqueous fluid ratio and determining a valley bottom of a distribution of the NMR response of the drilling fluid, wherein the distribution is a relaxation time distribution, and wherein the valley bottom separates an oleophilic signal from a water signal on the relaxation time distribution;
    selecting the oleophilic to aqueous fluid ratio as the oleophilic fluid to aqueous fluid ratio of the drilling fluid
    returning the sample of the drilling fluid used in the fluid analysis system to the drilling fluid; and
    adjusting an amount of one or more drilling fluid additives in the drilling fluid based in part to the oleophilic to aqueous fluid ratio before introducing into the wellbore.

12. A method according to claim 11, further comprising adjusting the oleophilic fluid to aqueous fluid ratio of the drilling fluid in response to the selecting the oleophilic fluid to aqueous fluid ratio.

13. A method according to claim 11, further comprising circulating the drilling fluid in the wellbore.

14. A method according to claim 11, further comprising adding drilling fluid additives to the drilling fluid in response to the selecting the oleophilic to aqueous ratio.

15. A drilling fluid monitoring and handling system comprising:
    a mud pit coupled to a wellbore, wherein the mud pit is configured to receive a drilling fluid exiting the wellbore; and
    a fluid analysis system coupled to the mud pit, wherein the fluid analysis system comprises a nuclear magnetic resonance (NMR) spectrometer, wherein the fluid analysis system is configured to measure and analyze an NMR response of a sample of the drilling fluid, wherein the fluid analysis system is configured to determine a valley bottom of a distribution of the NMR response of the drilling fluid, wherein the distribution is a relaxation time distribution, and wherein the valley bottom separates an oleophilic signal from a water signal on the relaxation time distribution; and wherein the fluid analysis system is configured to selectively adjust a relaxation rate of an aqueous phase of the sample of the drilling fluid.

16. A system according to claim 15, wherein the fluid analysis system is configured to compute an oleophilic fluid to aqueous fluid ratio of the drilling fluid.

17. A system according to claim 15, further comprising a flow line disposed between the mud pit and the fluid analysis system that provides samples of the drilling fluid to the mud pit.

18. A system according to claim 15, further comprising a return line disposed between the mud pit and the fluid analysis system that returns samples of the drilling fluid to the mud pit.

* * * * *